(12) United States Patent
Wang et al.

(10) Patent No.: US 11,278,207 B2
(45) Date of Patent: Mar. 22, 2022

(54) SYSTEM AND METHOD FOR PROVIDING MULTI-WAVELENGTH LASER FOR FAST FUNCTIONAL PHOTOACOUSTIC MICROSCOPY

(71) Applicant: City University of Hong Kong, Kowloon (HK)

(72) Inventors: Lidai Wang, Kowloon (HK); Yizhi Liang, Kowloon (HK)

(73) Assignee: City University of Hong Kong, Kowloon (HK)

( * ) Notice: Subject to any disclaimer, the term of this patent is extended or adjusted under 35 U.S.C. 154(b) by 301 days.

(21) Appl. No.: 15/493,283

(22) Filed: Apr. 21, 2017

(65) Prior Publication Data

US 2018/0303349 A1   Oct. 25, 2018

(51) Int. Cl.
| | |
|---|---|
| *A61B 5/00* | (2006.01) |
| *H01S 3/23* | (2006.01) |
| *G01N 21/65* | (2006.01) |
| *G01N 29/24* | (2006.01) |
| *H01S 3/30* | (2006.01) |
| *H01S 3/00* | (2006.01) |

(52) U.S. Cl.
CPC ........... *A61B 5/0095* (2013.01); *G01N 21/65* (2013.01); *G01N 21/658* (2013.01); *G01N 29/2418* (2013.01); *H01S 3/2391* (2013.01); *H01S 3/005* (2013.01); *H01S 3/302* (2013.01)

(58) Field of Classification Search
CPC ..... A61B 5/0095; H01S 3/005; H01S 3/2391; H01S 3/302; G01N 21/65; G01N 21/658; G01N 29/2418

USPC ........................................................ 600/407
See application file for complete search history.

(56) References Cited

U.S. PATENT DOCUMENTS

| | | | |
|---|---|---|---|
| 9,046,492 B1* | 6/2015 | Prater ................. | G01N 21/658 |
| 2003/0182013 A1* | 9/2003 | Moreas ............ | G01N 21/8901 700/145 |
| 2005/0244119 A1* | 11/2005 | Sasaki ................ | C03B 19/1453 385/123 |
| 2006/0187537 A1* | 8/2006 | Huber .................... | H01S 3/106 359/337.22 |

(Continued)

OTHER PUBLICATIONS

Liang, Yizhi, Jin, Long, Guan, Bai-Ou, and Wang, Lidai. 2 MHz multi-wavelength pulsed laser for functional photoacoustic microscopy [online]. Optics Letters, Mar. 31, 2017 [retrieved on Jun. 3, 2019], vol. 42, No. 7, pp. 1452-1455. Retrieved from the Internet: see office action for URL and DOI.*

(Continued)

*Primary Examiner* — Amanda Lauritzen Moher
(74) *Attorney, Agent, or Firm* — Renner Kenner Greive Bobak Taylor & Weber

(57) ABSTRACT

A system for providing multi-wavelength laser includes an optical splitter arranged to split light received from a pulsed laser source into at least a first light beam and a second light beam; a first optical regulator arranged to adjust a wavelength of the first light beam and to output the adjusted first light beam; a second optical regulator arranged to introduce a time delay to the second light beam and to output the delayed second light beam; and an optical combiner arranged to combine the adjusted first light beam and the delayed second light beam, and to output a combined light beam.

19 Claims, 5 Drawing Sheets

(56) References Cited

U.S. PATENT DOCUMENTS

| | | | | |
|---|---|---|---|---|
| 2014/0142404 A1* | 5/2014 | Wang | ............... | A61B 8/4416 |
| | | | | 600/324 |
| 2014/0160442 A1* | 6/2014 | Lee | ............... | H01S 3/302 |
| | | | | 353/38 |
| 2014/0247448 A1* | 9/2014 | Wise | ............... | G01N 21/65 |
| | | | | 356/301 |
| 2015/0355444 A1* | 12/2015 | Jiang | ............... | G02B 21/0028 |
| | | | | 359/385 |
| 2016/0113507 A1* | 4/2016 | Reza | ............... | G01N 21/1702 |
| | | | | 356/477 |

OTHER PUBLICATIONS

Wang, Tianxiong et al. Multiparametric photoacoustic microscopy of the mouse brain with 300-kHz A-line rate [online]. Neurophotonics, Nov. 30, 2016 [retrieved on Jun. 4, 2019], vol. 3, No. 4, pp. 045006-1 through 0405006-6. Retrieved from the Internet: see office action for URL and DOI.*

Lefrancois, Simon, et al. Fiber four-wave mixing source for coherent anti-Stokes Raman scattering microscopy [online]. Optics Letters, May 9, 2012 [retrieved on Jun. 4, 2019], vol. 37, No. 10, pp. 1652-1654. Retrieved from the Internet: see office action for URL and DOI.*

Horn, Alexander. Ultra-fast Material Metrology [online]. Wiley-VCH, 2009 [retrieved on Jun. 5, 2019], ISBN 978-3-527-40887-0, p. 114. Retrieved from the Internet: see office action for URL.*

Kumar, Sunil, et al. Single-pulse CARS based multimodal nonlinear optical microscope for bioimaging [online]. Optics Express, May 8, 2015 [retrieved on Jun. 4, 2019], vol. 23, No. 10, pp. 13082-13098. Retrieved from the Internet: see office action for URL and DOI.*

Hajireza, Parsin et al. In-vivo functional optical-resolution photoacoustic microscopy with stimulated Raman scattering fiber-laser source [online]. Biomedical Optics Express, Jan. 16, 2014 [retrieved on Jun. 5, 2019], vol. 5, No. 2, pp. 539-546. Retrieved from the Internet: see office action for URL and DOI.*

532 nm 20 W Fiber Laser « VPFL-G-20 » [online]. Laser Selection, earliest available capture dated Apr. 24, 2018 [retrieved on Dec. 15, 2020]. Retrieved from the Internet: <URL: https://web.archive.org/web/20180424093554/http://laser.photoniction.com/product/1780>.*

Hariri, Ali, et al. Towards ultrahigh resting-state functional connectivity in the mouse brain using photoacoustic microscopy [online]. Proc. SPIE 9708, Photons Plus Ultrasound: Imaging and Sensing 2016, Mar. 22, 2016 (retrieved on Dec. 15, 2020), pp. 97085A-1 to 97085A-4. Retrieved from the Internet. (Year: 2016).*

\* cited by examiner

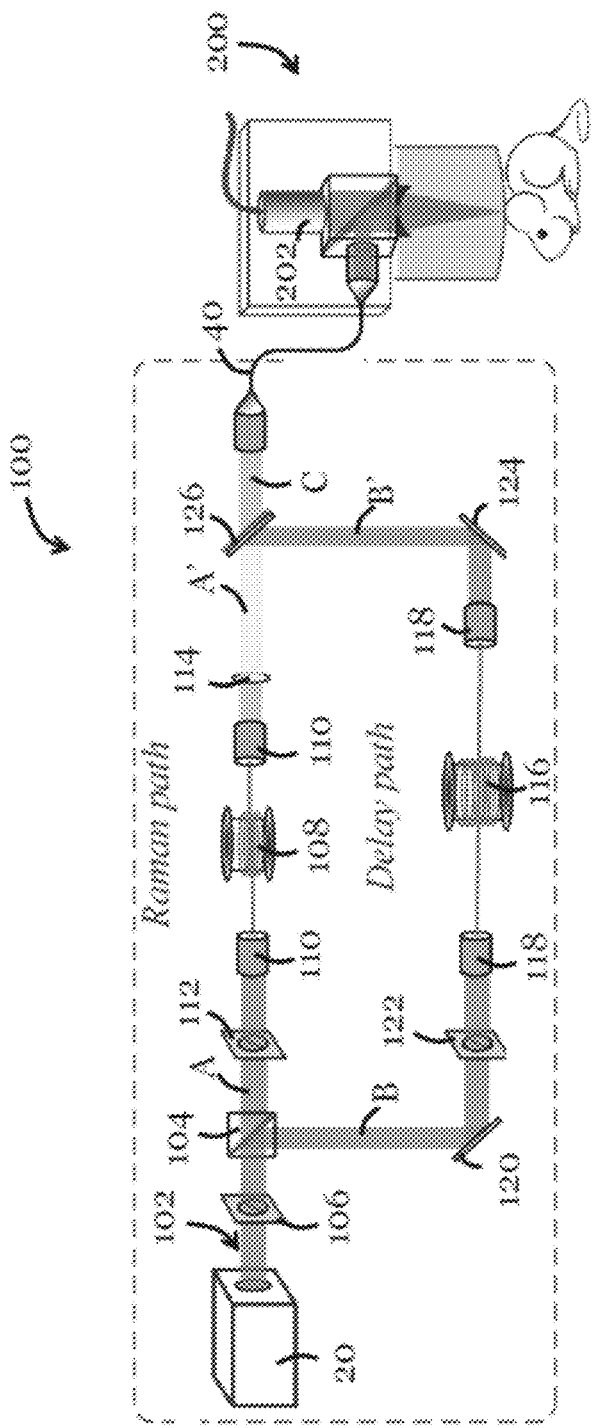
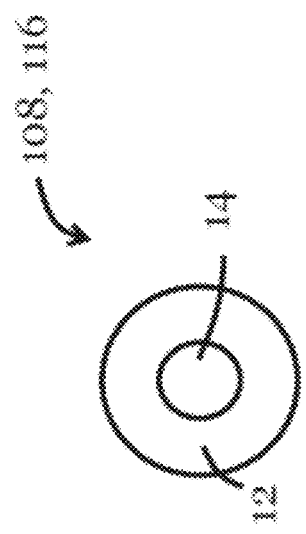
Figure 1a
Figure 1b

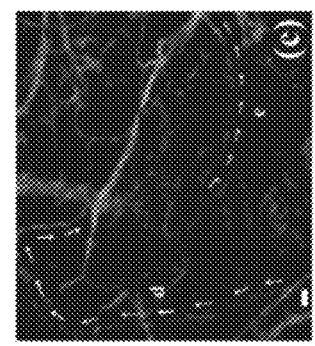
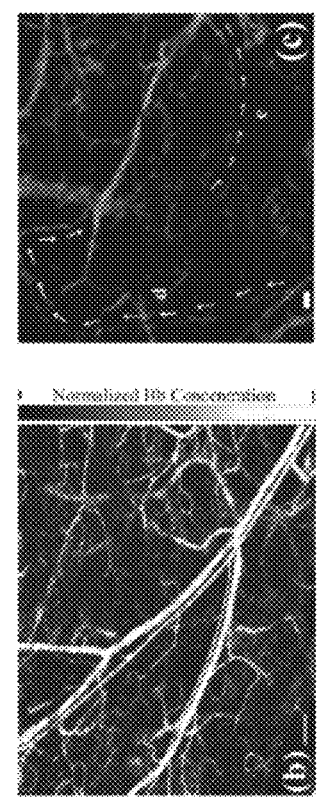
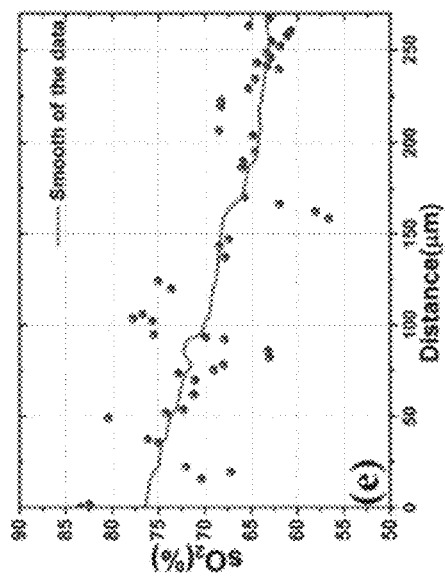
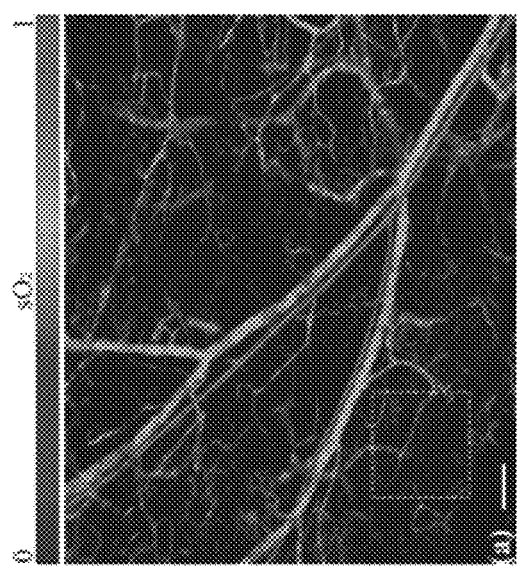
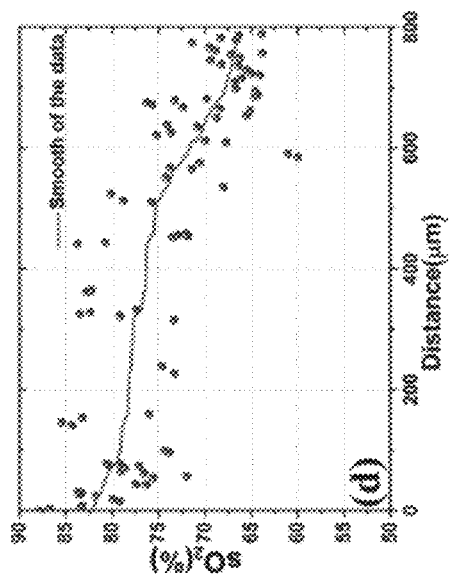
Figure 5a
Figure 5b
Figure 5c
Figure 5d
Figure 5e

SYSTEM AND METHOD FOR PROVIDING MULTI-WAVELENGTH LASER FOR FAST FUNCTIONAL PHOTOACOUSTIC MICROSCOPY

TECHNICAL FIELD

The present invention relates to a system and method for providing multi-wavelength laser, and particularly, although not exclusively, to a multi-wavelength pulsed laser source adapted for functional photoacoustic microscopy.

BACKGROUND

Photoacoustic imaging is a new biomedical imaging modality based on the use of laser-generated ultrasound, and it is considered as one of the most promising imaging techniques to have emerged in recent years.

In general, photoacoustic imaging is based on absorption of laser light by specific tissue chromophores to excite ultrasound waves. These ultrasonic waves are encoded with optical properties of the tissue. By recording these waves over the tissue surface, a 3D absorption based image can be reconstructed.

Photoacoustic imaging is advantageous in a number of aspects. Firstly, it is noninvasive and so is relatively safe to use in in vivo applications. Secondly, by encoding optical absorption into acoustic waves, the spatial resolution and/or penetration depth limitations associated with traditional optical imaging techniques (such as light microscopy or diffuse optical tomography) can be overcome. Being able to provide high molecular based contrast and spectral specificity of optical methods, photoacoustic imaging further facilitates visualization of anatomical features not obtainable with other imaging modalities (such as ultrasound).

SUMMARY OF THE INVENTION

In accordance with a first aspect of the present invention, there is provided a system for providing multi-wavelength laser, comprising: an optical splitter arranged to split light received from a pulsed laser source into at least a first light beam and a second light beam; a first optical regulator arranged to adjust a wavelength of the first light beam and to output the adjusted first light beam; a second optical regulator arranged to introduce a time delay to the second light beam and to output the delayed second light beam; and an optical combiner arranged to combine the adjusted first light beam and the delayed second light beam, and to output a combined light beam.

In one embodiment of the first aspect, the system further comprises the pulsed laser source. Preferably, the pulsed laser source is a nano-second pulsed laser. In one embodiment of the first aspect, an energy of the light provided by the pulsed laser source is adjustable.

In one embodiment of the first aspect, the system further comprises a power adjuster to adjust an energy ratio of the first light beam and the second light beam. The power adjuster may be arranged upstream of the optical splitter. Preferably, the power adjuster comprises a half-wave plate.

In one embodiment of the first aspect, the optical splitter comprises a polarizing beam splitter arranged to split the light into the first and second light beams based on polarization state.

In one embodiment of the first aspect, the system further comprises a polarization adjuster arranged between the optical splitter and the first optical regulator, for adjusting a polarization state of the first light beam. Preferably, the polarization adjuster comprises a half-wave plate.

In one embodiment of the first aspect, the first optical regulator comprises a single mode fiber arranged to adjust the wavelength of the first light beam by excitation based on stimulated Raman scattering.

In one embodiment of the first aspect, the single mode fiber of the first optical regulator is arranged to adjust wavelength of the first light beam to a wavelength with order higher than a first order stoke wavelength.

In one embodiment of the first aspect, the system further comprises a filter arranged downstream of the first optical regulator to control wavelength of the adjusted first light beam. Preferably, the filter is a band-pass filter.

In one embodiment of the first aspect, the system further comprises a polarization adjuster arranged between the optical splitter and the second optical regulator, for adjusting a polarization state of the second light beam. Preferably, the polarization adjuster comprises a half-wave plate.

In one embodiment of the first aspect, the second optical regulator comprises a single mode fiber.

In one embodiment of the first aspect, the single mode fiber of the second optical regulator is further arranged to alter wavelength of only part of the second light beam based on stimulated Raman scattering. In a preferred embodiment, the single mode fiber of the second optical regulator is arranged to alter wavelength of said part of the second light beam to a first order stoke wavelength, and more preferably, only to the first order stoke wavelength.

In one embodiment of the first aspect, the optical combiner comprises a dichroic mirror.

In a preferred embodiment of the first aspect, the single mode fiber of the first optical regulator is formed with a pure silica core surrounded by a cladding.

In a preferred embodiment of the first aspect, the single mode fiber of the second optical regulator is formed with a pure silica core surrounded by a cladding.

In accordance with a second aspect of the present invention, there is provided a photoacoustic imaging apparatus, comprising: a system for providing multi-wavelength laser and an imaging system with an imaging probe operably connected with the system. The system for providing multi-wavelength laser comprises an optical splitter arranged to split light received from a pulsed laser source into at least a first light beam and a second light beam; a first optical regulator arranged to adjust a wavelength of the first light beam and to output the adjusted first light beam; a second optical regulator arranged to introduce a time delay to the second light beam and to output the delayed second light beam; and an optical combiner arranged to combine the adjusted first light beam and the delayed second light beam, and to output a combined light beam. The imaging system receives the combined light beam for imaging.

In one embodiment of the second aspect, the photoacoustic imaging apparatus further comprises a single mode fiber for connecting the system with the imaging system.

In one embodiment of the second aspect, the system further comprises the pulsed laser source. Preferably, the pulsed laser source is a nano-second pulsed laser. In one embodiment of the first aspect, an energy of the light provided by the pulsed laser source is adjustable.

In one embodiment of the second aspect, the system further comprises a power adjuster to adjust an energy ratio of the first light beam and the second light beam. The power adjuster may be arranged upstream of the optical splitter. Preferably, the power adjuster comprises a half-wave plate.

In one embodiment of the second aspect, the optical splitter comprises a polarizing beam splitter arranged to split the light into the first and second light beams based on polarization state.

In one embodiment of the second aspect, the system further comprises a polarization adjuster arranged between the optical splitter and the first optical regulator, for adjusting a polarization state of the first light beam. Preferably, the polarization adjuster comprises a half-wave plate.

In one embodiment of the second aspect, the first optical regulator comprises a single mode fiber arranged to adjust the wavelength of the first light beam by excitation based on stimulated Raman scattering.

In one embodiment of the second aspect, the single mode fiber of the first optical regulator is arranged to adjust wavelength of the first light beam to a wavelength with order higher than a first order stoke wavelength.

In one embodiment of the second aspect, the system further comprises a filter arranged downstream of the first optical regulator to control wavelength of the adjusted first light beam. Preferably, the filter is a band-pass filter.

In one embodiment of the second aspect, the system further comprises a polarization adjuster arranged between the optical splitter and the second optical regulator, for adjusting a polarization state of the second light beam. Preferably, the polarization adjuster comprises a half-wave plate.

In one embodiment of the second aspect, the second optical regulator comprises a single mode fiber.

In one embodiment of the second aspect, the single mode fiber of the second optical regulator is further arranged to alter wavelength of only part of the second light beam based on stimulated Raman scattering. In a preferred embodiment, the single mode fiber of the second optical regulator is arranged to alter wavelength of said part of the second light beam to a first order stoke wavelength, and more preferably, only to the first order stoke wavelength.

In one embodiment of the second aspect, the optical combiner comprises a dichroic mirror.

In a preferred embodiment of the second aspect, the single mode fiber of the first optical regulator is formed with a pure silica core surrounded by a cladding.

In a preferred embodiment of the second aspect, the single mode fiber of the second optical regulator is formed with a pure silica core surrounded by a cladding.

In accordance with a third aspect of the present invention, there is provided a method for providing multi-wavelength laser, comprising: splitting light received from a pulsed laser source into at least a first light beam and a second light beam; adjusting a wavelength of the first light beam so as to provide the adjusted first light beam; regulating the second light beam by introducing a time delay thereto so as to provide the delayed second light beam; and combining the adjusted first light beam and the delayed second light beam to form a combined light beam.

In one embodiment of the third aspect, the method further comprises adjusting an energy of the light provided by the pulsed laser source.

In one embodiment of the third aspect, the method further comprises adjusting an energy ratio of the first and second light beams.

In one embodiment of the third aspect, the splitting step is performed based on based on polarization state of the first and second light beams.

In one embodiment of the third aspect, the method further comprises adjusting a polarization state of the first light beam, prior to the wavelength adjustment step for the first light beam.

In one embodiment of the third aspect, the wavelength adjustment step for the first light beam is performed via excitation based on stimulated Raman scattering.

In one embodiment of the third aspect, the wavelength adjustment step is arranged to adjust wavelength of the first light beam to a wavelength with order higher than a first order stoke wavelength.

In one embodiment of the third aspect, the method further comprises filtering the light beam obtained after the wavelength adjustment step for the first light beam to provide the adjusted first light beam.

In one embodiment of the third aspect, the method further comprises adjusting a polarization state of the second light beam, prior to the regulation step for the second light beam.

In one embodiment of the third aspect, regulation step for the second light beam further comprises altering wavelength of only part of the second light beam based on stimulated Raman scattering. In a preferred embodiment, the wavelength of said part of the second light beam is altered to a first order stoke wavelength, and more preferably, only to the first order stoke wavelength.

In one embodiment of the third aspect, the method further comprises providing the combined light beam to an imaging apparatus.

In accordance with a fourth aspect of the present invention, there is provided a system for providing multi-wavelength laser, comprising: a first optical regulator arranged to adjust a wavelength of a first laser beam and to output the adjusted first light beam; a second optical regulator arranged to introduce a time delay to a second laser beam and to output the delayed second light beam; and an optical combiner arranged to combine the adjusted first light beam and the delayed second light beam, and to output a combined light beam; wherein the first and second laser beams are pulsed laser beams and are initially of the same wavelength.

In one embodiment of the fourth aspect, the first and second laser beams are received from the same pulsed laser source. In some examples, however, the first and second laser beams may be received from different laser sources.

In one embodiment of the fourth aspect, the system further comprises an optical splitter arranged to split light received from a pulsed laser source into at least the first light beam and the second light beam.

In one embodiment of the fourth aspect, the system further includes one or more other features in the first aspect.

The system, apparatus, and method in the above aspects of the invention are particularly suitable for use in functional photoacoustic microscopy.

BRIEF DESCRIPTION OF THE DRAWINGS

Embodiments of the present invention will now be described, by way of example, with reference to the accompanying drawings in which:

FIG. 1a is a schematic block diagram showing a system for providing multi-wavelength laser in accordance with one embodiment of the present invention, coupled with an exemplary photoacoustic imaging system;

FIG. 1b is a cross sectional view of a single mode fiber used in the system of FIG. 1a;

FIG. 2a is a graph showing an optical spectrum of the laser generated by the system of FIG. 1a;

FIG. 2b is a graph showing a temporal spectrum of the laser generated by the system of FIG. 1a;

FIG. 5a is an image showing in vivo oxygen saturation in a mouse ear (scale bar=200 μm);

FIG. 5b is an image corresponding to FIG. 5a, showing a total hemoglobin concentration in the mouse ear (scale bar=200 μm);

FIG. 5c is an image showing a zoomed-in view of the dashed box area in FIG. 5a (scale bar=20 μm);

FIG. 5d is a graph showing the measured $sO_2$ value as a function of the position along one capillaries identified in FIG. 5c; and FIG. 5e is a graph showing the measured $sO_2$ value as a function of the position along another capillary identified in FIG. 5c.

DETAILED DESCRIPTION OF THE PREFERRED EMBODIMENT

Figure 2A:
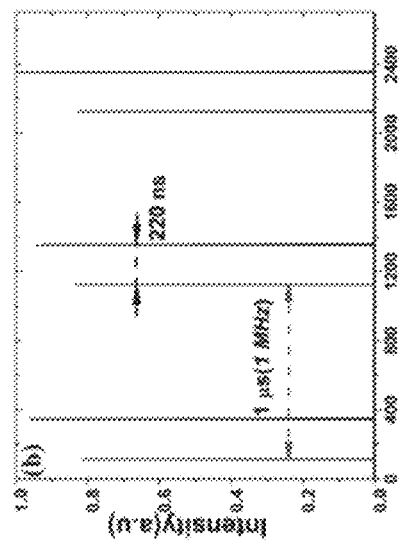

The inventors of the present invention have devised, through research, experiments and trials, that high-speed functional photoacoustic imaging—optical-resolution photoacoustic microscopy (OR-PAM)—requires laser sources with multiple wavelengths, sufficient pulse energy for each wavelength, and short switching time among different wavelengths.

The inventors of the present invention have devised that laser pulse repetition rate is one of the major bottlenecks for fast OR-PAM. For applications in sO2 imaging, at least two excitation wavelengths are required and this requires a doubled laser pulse repetition rate. On the other hand, the delay time between the pulses of the two different wavelengths is the laser pulse repetition time, which may be problematic when scanning fast. Also, ideally, the wavelength switching time should be much shorter than the pulse repetition time of the same wavelength to avoid misalignment problems.

FIG. 1a shows a system for providing multi-wavelength laser in accordance with one embodiment of the present invention coupled with an exemplary photoacoustic imaging system. For simplicity, only the main functional components are illustrated.

The system 100 is FIG. 1a can be considered as a multi-wavelength laser source. It comprises an input 102 arranged to receive light from a laser source 20 in the form of a pump laser. The laser source 20 is preferably a pulsed laser source. Energy of the light provided by the pulsed laser source 20 may be adjustable. In the present embodiment, the laser source 20 is a 532-nm nano-second pulsed laser (VPFL-G-20, SPECTRA PHYSICS™) In this example, the highest pulse repetition rate of the laser source is 1 MHz, and the average power can reach 20 W.

As shown in FIG. 1, the beam received from the laser source 20 is split by an optical splitter 104 into two light beams in separate paths—a Raman path and a delay path. In the present embodiment, the optical splitter 104 is a polarizing beam splitter arranged to split the light into first and second light beams A, B based on polarization state. Optionally, a power adjuster 106 may be arranged to adjust the energy ratio between the two paths/beams A, B. In the present embodiment, the power adjuster 106 comprises a half-wave plate. In other embodiments, however, the power adjuster 106 may be formed by one or more quarter-wave plate, half-wave plate, or their combination. In the present example, the power adjuster 106 is arranged upstream of the splitter but in other cases the power adjuster 106 may be arranged downstream of the splitter in one or both of the paths.

In the present embodiment, in the Raman path (upper path), the first laser beam A (532 nm in this example) is coupled into an optical regulator in the form of a single-mode fiber (HB450-SC, FIBERCORE™) 108 with a fiber launcher (MBT621D/M, THORLABS INC™) or couplers 110. In this example, the single-mode fiber 108 is a 5-meter-long polarization maintaining fiber, the coupling efficiency is above 60%, and the numerical aperture of the fiber is 0.12. Preferably, in the Raman path, the stimulated Raman scattering (SRS) effect partially converts the pump energy to first and higher order stoke wavelengths. In this example, the first and higher order stoke wavelengths are 545 nm and 558 nm respectively.

Optionally, a polarization adjuster 112 is arranged in front of the fiber 108 to tune the input polarization state to affect the SRS efficiency. In this example, a half-wave plate is used as the polarization adjuster 112.

The energy of the 558-nm laser can be optimized by adjusting the pump energy and polarization state. Preferably, a filter 114 may be arranged at the output of the fiber 108 to select the higher order stoke wavelength (e.g., 558 nm). In the present example, the filter 114 is a bandpass filter centered at 560 nm with a bandwidth of 10 nm (FB560-10, THORLABS INC™). In other embodiments, the filter 114 may be a band-stop, low-pass, high-pass or other filters suitable for filtering lights with unwanted wavelengths.

In the delay path, the second laser beam (532 nm in this example) B is coupled into an optical regulator in the form of a single-mode fiber (HB450-SC, FIBERCORE™) 116 with a fiber launcher (MBT621D/M, THORLABS INC™) or couplers 118, e.g., via a mirror 120 arranged between the beam splitter 104 and the fiber 116. In this example, the single-mode fiber 116 is a 50-meter-long single-mode fiber for introducing time delay. Similar as that in the Raman path, the input energy, and polarization state are carefully controlled, through the use of a polarization adjuster 122. In one example, the polarization adjuster 122 is a half-wave plate. In the present embodiment, the delay path is arranged to suppress the SRS effect. In this respect, the single mode fiber 116 is arranged to alter wavelength of part of the second light beam to a first order stoke wavelength, and more preferably, only to the first order stoke wavelength. As such only the first stokes wavelength (545 nm) is excited at the delay path. A mirror 124 may be arranged at the output of the fiber 116 in the delay path to direct the delayed light into an optical combiner 126.

In FIG. 1a, the optical combiner 126 is a dichroic mirror (T550lpxr-UF1, CHROMA™) arranged to combine the adjusted first light beam A' and the delayed second light beam B', and to output a combined light beam C. In this example, it combines the Raman beam (558 nm) with the delayed beam (532/545 nm).

Preferably, the combined beam C is operably connected to an OR-PAM imaging probe 200 via, e.g., a single-mode fiber 40. In this example, the single mode fiber 40 is 2 meters long. The imaging probe 200 may include or be coupled with an ultrasonic transducer 202.

In the OR-PAM probe 200, the multi-wavelength beams are focused to targets to excite photoacoustic signals. An optical/acoustic beam combiner (not shown) may be used to coaxially and confocally align the optical excitation and acoustic detection beams so that an optimized photoacoustic sensitivity can be achieved. Two translational stages raster may be used to operate the imaging probe to acquire volumetric photoacoustic images.

In an alternative embodiment, the first laser beam A and the second laser beam B of the same wavelength may be received from separate pulsed laser sources that preferably have similar or the same characteristics. In such case, the optical splitter may be omitted.

FIG. 1*b* shows a cross sectional view of a single mode fiber 108, 116 used in the Raman path and/or the delay path of the system in FIG. 1*a*. In the present embodiment, the fiber 108, 116 generally includes a core 14 surrounded by a cladding 12. The core 14 is preferably a pure silica core, as opposed to conventional Germanium-doped ones. This is advantageous because the optical fiber for SRS might be damaged by either a high peak power or a high pulse repetition rate of the pump laser, and so the Germanium dopant in conventional fibers may cause irreversible damage via the photo-darkening effect at 532 nm at an average power of a few hundred milliwatts at 1 MHz pulse repetition rate. In contrast, the pure-silica core fiber in the present embodiment can handle at least 8 W at the same pulse repetition rate, which allows enough pulse energy at a high pulse repetition rate for both Raman and delay paths. In addition, the polarization-maintaining fiber can improve the efficiency and lower the threshold of SRS.

FIG. 2*a* shows the optical spectrum of the multi-wavelength laser produced by the source in FIG. 1*a* measured with an optical spectrometer (USB 2000+, OCEAN OPTICS™) SRS converts the 532 nm light to longer wavelengths as a result of inelastic scattering in the optical fiber. In this example, the maximum Raman scattering efficiency of the single-mode fiber occurs at a frequency shift of ~13.2 THz, corresponding to a ~13-nm wavelength interval near 532 nm. The line widths for the 532, 545 and 558 nm are 0.85, 2.20 and 3.14 nm respectively. Although the line widths of the higher order stokes wavelengths are broadened, they are still acceptable for sO2 imaging. The molar extinction coefficients of Hb and HbO2 are superimposed in FIG. 2*a*. As shown, the first stokes wavelength of 545 nm is an isosbestic point for Hb and HbO2. At the second stokes wavelength 558 nm, Hb absorbs light much stronger than HbO2.

Figure 2B:
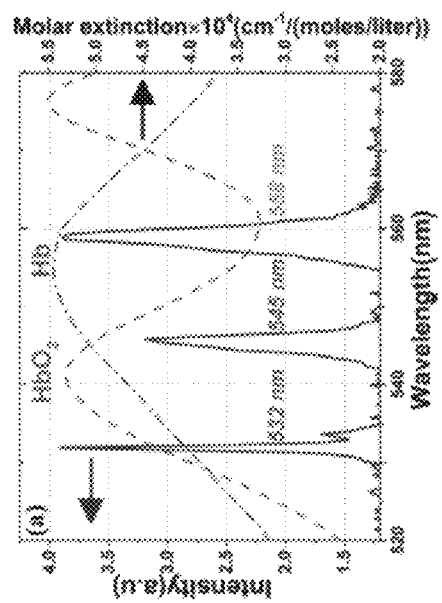

FIG. 2*b* shows the combined Raman and delayed pulses measured with a high-speed photo-detector and a DAQ card. As shown, the pulse width of the pump laser is 3 ns. The total pulse repetition rate for both 558-nm and 532/545-nm wavelengths is 2 MHz. The optical delay line separates the two pulses by 220 ns.

Figure 3A:
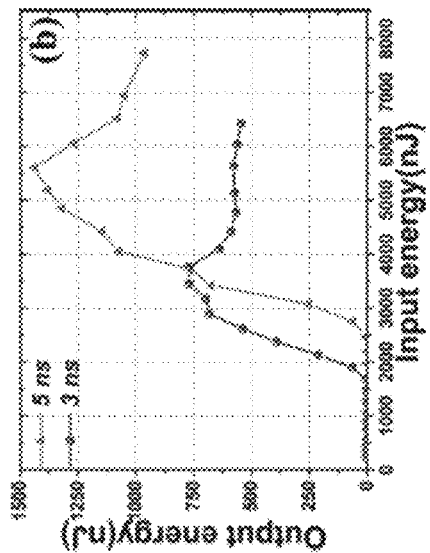
FIG. 3a is a graph showing the output energy of the laser in the delay path in the system of FIG. 1a for different input pulse widths and energies.

As it shows in FIG. 3*a*, the maximum allowed output pulse energy in the delay path is determined by the Raman threshold. Because the pump (532 nm) and the first stokes wavelength (545 nm) are near isosbestic points for Hb and HbO2, both wavelengths are used in this example for the delayed pulse. The input pulse width also affects the SRS threshold. A shorter pulse has a higher peak power. FIG. 3*a* shows that the 3-ns pulse has a lower maximum output pulse energy than the 5-ns one. For the 50-m delay line, the SRS thresholds of the 558-nm wavelength are ~125 nJ at the 3-ns pulse width, and ~175 nJ at the 5-ns pulse width, both of which are sufficient for most in vivo OR-PAM imaging. FIGS. 3(*c*) and 3(*e*) show enlarged views of the delayed 5-ns and 3-ns pulses. The delayed pulses maintain almost the same pulse widths with their pump widths.

Figure 3B:
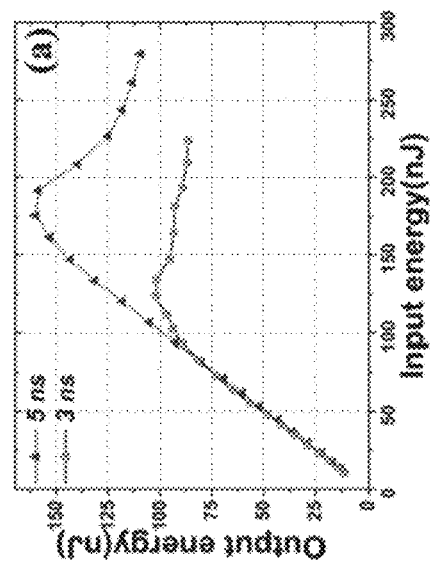
FIG. 3b is a graph showing the output energy of the laser in the Raman path in the system of FIG. 1a for different input pulse widths and energies.
Figure 3C:
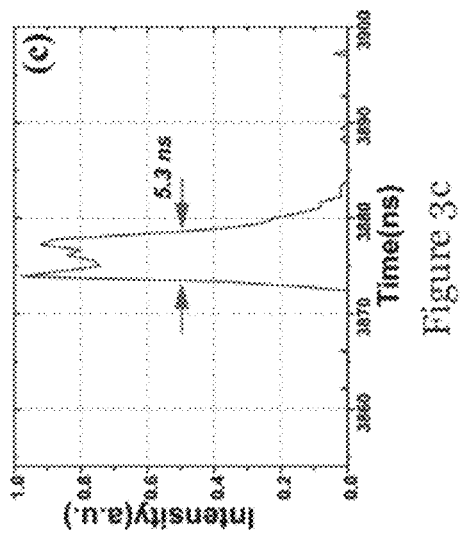
FIG. 3c is a graph showing the output pulse waveform of the delay path of FIG. 1a with input pulse width of 5 ns.

FIG. 3*b* shows the measured outputs of the Raman path at different input powers and pulse widths. In the present example, a 5-meter fiber is used to generate the 558-nm pulses. Raman-shifted wavelengths have higher thresholds and higher output energies in a shorter optical fiber. Similar to the delay path, the input power and polarization are optimized. For the maximum output of the 558-nm wavelength, the input pulse energy needs to be right below the threshold for generating the next stokes wavelength. The pulse width also affects the SRS threshold. For the 3-ns and 5-ns pulses, the thresholds to generate 558-nm wavelength are 3.5 µJ and 5.5 µJ respectively. A shorter pulse width has a lower threshold and a higher photoacoustic excitation efficiency, but the maximum output energy of the stokes wavelength is lower too.

Figure 3D:
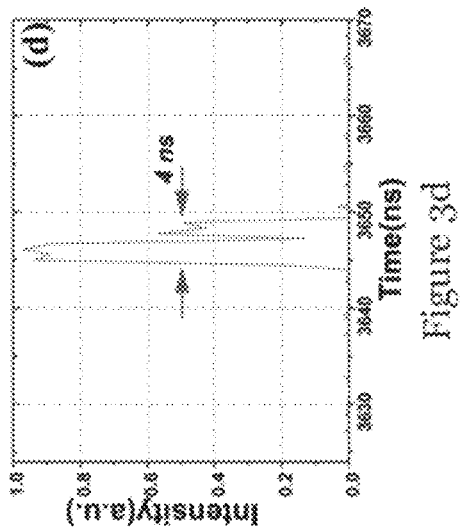
FIG. 3d is a graph showing the output pulse waveform of the Raman path of FIG. 1a with input pulse width of 5 ns.
Figure 3E:
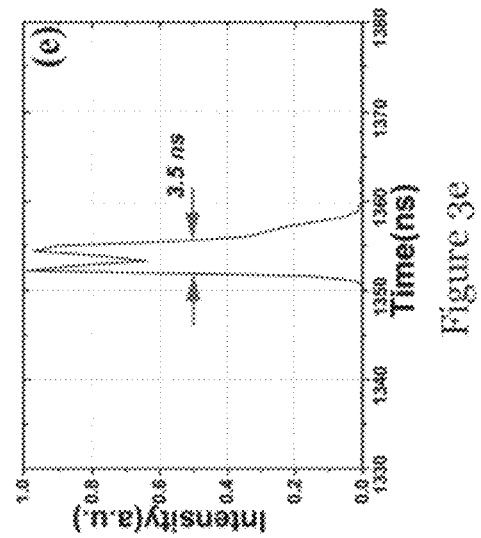
FIG. 3e is a graph showing the output pulse waveform of the delay path of FIG. 1a with input pulse width of 3 ns.
Figure 3F:
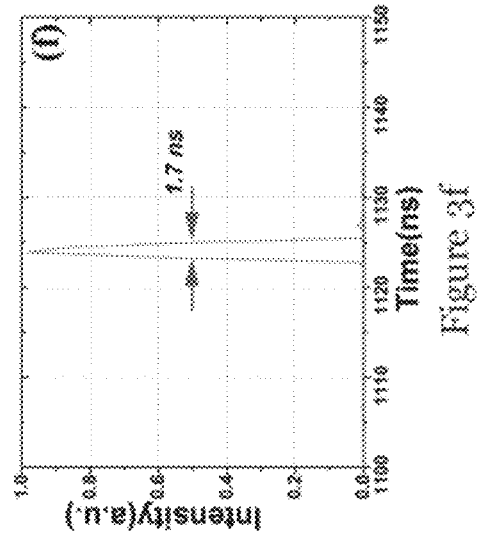
FIG. 3f is a graph showing the output pulse waveform of the Raman path of FIG. 1a with input pulse width of 3 ns.

As shown in FIGS. 3*d* and 3*f*, the 558-nm pulse becomes narrower compared to the pump pulses due to the nonlinear SRS effect. In nanosecond range, shorter pulses may generate stronger (or more high frequency) photoacoustic signals. Thus the narrowed 558-nm pulses may benefit the sensitivity of photoacoustic imaging.

To maximize the output power of the Nth-order Raman stokes wavelength, the pump power can be described as $$P_N^{Max} \approx 30 * N * A_{eff}/(g_R L_{eff}) \exp(-\alpha L)$$

where the $A_{eff}$ is the effective mode area of the pump light in the fiber, the $g_R$ is the Raman gain coefficient, L is the fiber length, $\alpha$ is the fiber loss coefficient, and the $L_{eff}=(1-\exp(-\alpha L))/\alpha$ is the effective length.

As shown in the above equation, a low loss and a short fiber lead to a high pump and output power.

Figure 4:
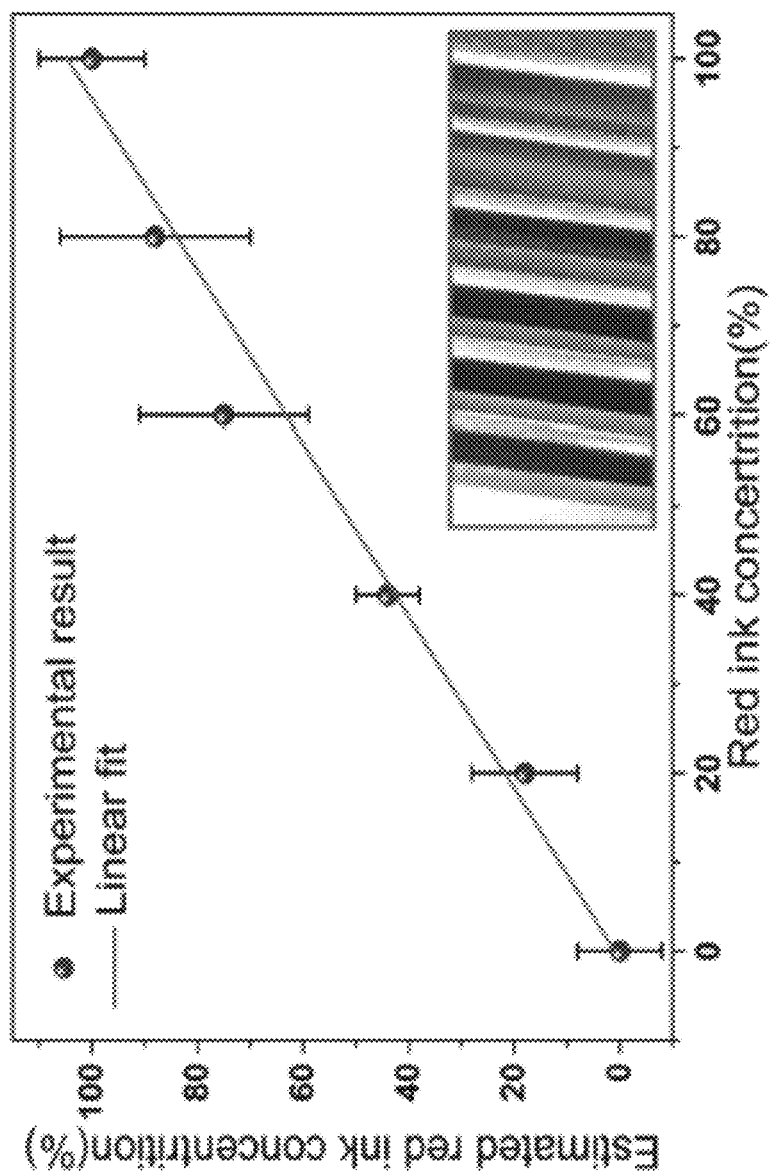
FIG. 4 is a plot showing an experimental result of photoacoustic measurement of red and blue ink concentrations using system of FIG. 1a as a laser source.

Using the developed multi-wavelength laser and an OR-PAM system as shown in FIG. 1*a*, multi-wavelength photoacoustic imaging experiments were performed on phantoms. In the experiment, red and blue inks are mixed in different volumetric ratios and are filled in transparent rubber tubes. The tubes were imaged with the OR-PAM system equipped with the new multi-wavelength laser of FIG. 1*a*. The volumetric ratios were calculated from a simple spectral un-mixing algorithm. FIG. 4 shows the measured results, which suggest a good agreement between the set and measured values.

FIG. 5 shows a specific application of the system in FIG. 1*a*—in vivo imaging of the micro-vascular structure and oxygen saturation in the mouse ear. In this example, the laser pulse energy was 65 nJ for both the 532+545-nm and the 558-nm pulses. A 2.5×2.5 mm2 region was raster scanned. FIG. 5*b* shows that the capillaries and single red blood cells can be clearly resolved with a high signal-to-noise ratio, indicating that the laser system provides enough energy for in vivo imaging. Using a simple spectral un-mixing method, the oxygen saturation of the blood vessels was quantified, results shown in the FIG. 5*a*. As shown, the arteries and veins can be clearly differentiated from each other. Benefited from the 220-ns wavelength switching time, the oxygen saturation even on single red blood cells can be and was calculated. As shown in the close-up view in FIG. 5*c*, the sO2 values along the capillaries gradually change from high to low when the red blood cells flow from the arterioles to the venules. The sO2 value is plotted as a function of the position along two capillaries in FIGS. 5d and 5e. Single red blood cells show gradually reduced oxygen saturations when flowing from arterioles to venules. The oxygen level in arterioles and venules is in good agreement with known physiological results. In the present example, the spatial oxygen release rates along the capillaries are quantified in vivo. The average oxygen release rate in the two capillaries is about 6% per 100 μm.

It is envisaged that the OR-PAM system in embodiments of the present invention may be used with different laser sources, such as but not limited to a 2-MHz laser source. Accordingly, high-speed functional photoacoustic images can be acquired efficiently and reliably.

Embodiments of the present invention have provided a new multi-wavelength pulsed laser particularly adapted for fast functional OR-PAM. Based on the SRS effect, multi-wavelength pulses can be generated at 2 MHz. By combining a Raman-shifted pulse with a fiber-delayed pulse, wavelength switching in 220 ns can be implemented. The laser source can generate at least 100-nJ pulse energy for each pulse. Embodiments of the present invention may be used in in vivo imaging of oxygen saturation on trunk blood vessels and single red blood cells, and it has great potential in a wide range of applications in functional photoacoustic imaging.

Embodiments of the present invention have provided an SRS-based multi-wavelength (532/545 nm+558 nm) fiber laser. Each wavelength has a pulse repetition rate of 1 MHz, equivalent to 2 million pulses per second for all wavelengths. A fiber delay line is employed to temporally separate the dual-wavelength pulses by 220 ns so that the excitation wavelengths can be switched pulse-by-pulse for fast functional photoacoustic imaging. The wavelength switching time can be readily adjusted via changing the length of the fiber delay line. Special design on the new fiber laser allows it to handle high laser power up to 1 W. The pulse energy for each wavelength can reach at least 100 nJ, which is sufficient for most in vivo OR-PAM imaging at these wavelengths. This technical advance fully exploits the high pulse repetition rate of the pump laser, providing an ideal laser source for fast functional OR-PAM imaging.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Any reference to prior art contained herein is not to be taken as an admission that the information is common general knowledge, unless otherwise indicated.

The invention claimed is:

1. A system for providing multi-wavelength laser for fast functional photoacoustic microscopy, comprising:
    a pulsed laser source arranged to provide a pulsed laser beam with a single wavelength;
    a polarizing beam splitter arranged to split the pulsed laser beam received from the pulsed laser source based on polarization state into at least a first pulsed laser beam with the single wavelength and a second pulsed laser beam with the single wavelength;
    a first optical regulator including a single mode fiber arranged to adjust the single wavelength of the first pulsed laser beam by excitation based on stimulated Raman scattering to a higher order stoke wavelength higher than a first order stoke wavelength and to output the adjusted first pulsed laser beam with the higher order stoke wavelength;
    a filter arranged downstream of the first optical regulator to control wavelength of the adjusted first pulsed laser beam to include only the higher order stoke wavelength;
    a second optical regulator including a single mode fiber arranged to introduce a time delay to the second pulsed laser beam, to alter wavelength of only part of the second pulsed laser beam to a first order stoke wavelength while maintaining the wavelength of the remaining part of the second pulsed laser beam to be at the single wavelength, and to output a delayed second pulsed laser beam with the single wavelength and the first order stoke wavelength; and
    an optical combiner arranged to combine the adjusted first pulsed laser beam with the higher order stoke wavelength and the delayed second pulsed laser beam with the single wavelength and the first order stoke wavelength and to output a combined pulsed laser beam with the single wavelength, the first order stoke wavelength, and the higher order stoke wavelength for the fast functional photoacoustic microscopy;
    wherein the pulsed laser source is the only laser source of the system.

2. The system of claim 1, wherein the filter is a band-pass filter.

3. The system of claim 1, wherein the optical combiner comprises a dichroic mirror.

4. The system of claim 1, wherein the single mode fiber of the first optical regulator is formed with a pure silica core surrounded by a cladding.

5. The system of claim 1, wherein the single mode fiber of the second optical regulator is formed with a pure silica core surrounded by a cladding.

6. The system of claim 1, wherein an energy of the pulsed laser beam received from the pulsed laser source is adjustable.

7. The system of claim 1, wherein the pulsed laser source is a nano-second pulsed laser source.

8. The system of claim 7, wherein the single wavelength is 532 nm, the first order stoke wavelength is 545 nm, and the higher order stoke wavelength is 558 nm.

9. The system of claim 1, further comprising a power adjuster to adjust an energy ratio of the first pulsed laser beam and the second pulsed laser beam.

10. The system of claim 9, wherein the power adjuster is arranged upstream of the optical splitter.

11. The system of claim 9, wherein the power adjuster comprises a half-wave plate.

12. The system of claim 1, further comprising a polarization adjuster arranged between the optical splitter and the first optical regulator, for adjusting a polarization state of the first pulsed laser beam.

13. The system of claim 12, wherein the polarization adjuster comprises a half-wave plate.

14. The system of claim 1, further comprising a polarization adjuster arranged between the optical splitter and the second optical regulator, for adjusting a polarization state of the second pulsed laser beam.

15. The system of claim 14, wherein the polarization adjuster comprises a half-wave plate.

16. A photoacoustic imaging apparatus, comprising:
    a laser-providing system for providing multi-wavelength laser for fast functional photoacoustic microscopy, the laser-providing system comprising:

a pulsed laser source arranged to provide a pulsed laser beam with a single wavelength;

a polarizing beam splitter arranged to split the pulsed laser beam received from the pulsed laser source based on polarization state into at least a first pulsed laser beam with the single wavelength and a second pulsed laser beam with the single wavelength;

a first optical regulator including a single mode fiber arranged to adjust the single wavelength of the first pulsed laser beam by excitation based on stimulated Raman scattering to a higher order stoke wavelength higher than a first order stoke wavelength and to output the adjusted first pulsed laser beam with the higher order stoke wavelength;

a filter arranged downstream of the first optical regulator to control wavelength of the adjusted first pulsed laser beam to include only the higher order stoke wavelength;

a second optical regulator including a single mode fiber arranged to introduce a time delay to the second pulsed laser beam and to alter wavelength of only part of the second pulsed laser beam to a first order stoke wavelength while maintaining the wavelength of the remaining part of the second pulsed laser beam to be at the single wavelength, and to output a delayed second pulsed laser beam with the single wavelength and the first order stoke wavelength; and an optical combiner arranged to combine the adjusted first pulsed laser beam with the higher order stoke wavelength and the delayed second pulsed laser beam with the single wavelength and the first order stoke wavelength, and to output a combined pulsed laser beam with the single wavelength, the first order stoke wavelength, and the higher order stoke wavelength for the fast functional photoacoustic microscopy; and an imaging system with an imaging probe operably connected with the laser-providing system to receive the combined light beam for imaging;

wherein the pulsed laser source is the only laser source of the laser-providing system.

17. The photoacoustic imaging apparatus of claim 16, further comprising a single mode fiber for connecting the laser-providing system with the imaging system.

18. The photoacoustic imaging apparatus of claim 16, wherein the pulsed laser source is a nano-second pulsed laser source.

19. The photoacoustic imaging apparatus of claim 18, wherein the single wavelength is 532 nm, the first order stoke wavelength is 545 nm, and the higher order stoke wavelength is 558 nm.

* * * * *